United States Patent [19]

Hanus

[11] Patent Number: 5,547,351
[45] Date of Patent: Aug. 20, 1996

[54] LOW PRESSURE LOW VOLUME LIQUID PUMP

[75] Inventor: James P. Hanus, Mesquite, Tex.

[73] Assignee: The United States of America as represented by the Secretary of the Department of Health and Human Services, Washington, D.C.

[21] Appl. No.: 203,781

[22] Filed: Mar. 1, 1994

[51] Int. Cl.⁶ .................................................. F04B 9/08
[52] U.S. Cl. ...................... 417/386; 417/395; 417/DIG. 1
[58] Field of Search ..................................... 417/386, 387, 417/395, DIG. 1

[56] References Cited

U.S. PATENT DOCUMENTS

| | | | |
|---|---|---|---|
| 862,867 | 8/1907 | Eggleston | 417/472 X |
| 2,303,597 | 12/1942 | Adelson | 417/386 X |
| 2,843,045 | 7/1958 | Mashinter | 417/386 X |
| 3,212,411 | 10/1965 | Storms | 417/DIG. 1 |
| 3,233,554 | 2/1966 | Huber et al. | 417/DIG. 1 |
| 3,779,669 | 12/1973 | Sommer | 417/387 X |
| 4,688,999 | 8/1987 | Ames | 417/DIG. 1 |
| 5,186,615 | 2/1993 | Karliner | 417/387 |
| 5,246,351 | 9/1993 | Horn et al. | 417/387 |
| 5,249,932 | 10/1993 | Van Bork | 417/386 |

FOREIGN PATENT DOCUMENTS

| | | | |
|---|---|---|---|
| 0214394 | 3/1987 | European Pat. Off. | 417/DIG. 1 |
| 1264613 | 5/1961 | France | 417/386 |

OTHER PUBLICATIONS

Cole-Parmer Instrument Company, Catatog 1985–1986 pp. 554–556.

Primary Examiner—Richard E. Gluck
Attorney, Agent, or Firm—Lowe, Price, Leblanc & Becker

[57] ABSTRACT

A diaphragm pump which provides a low internal volume and minimizes volume contributions for applications which require the transfer of fluid volumes on the order of one to several microliters. The pump includes a plunger which reciprocates within a bore and applies fluid pressure to a diaphragm of a head cavity that is connected to the cylinder bore. Hydraulic feed and vent passages connect to the cylinder bore at a point where the end of the plunger passes during reciprocal movement to ensure that the amount of hydraulic fluid within the cylinder bore is consistent during each stroke of the plunger. The pump is particularly useful for supplying receptor media to a Franz cell.

2 Claims, 2 Drawing Sheets

LOW PRESSURE LOW VOLUME LIQUID PUMP

TECHNICAL FIELD

The present invention relates to diaphragm pumps and more particularly to diaphragm pumps which are especially useful in automatic drug release testing systems. The present invention further relates to automatic drug release testing systems and methods.

BACKGROUND ART

The Food and Drug Administration (FDA) has recently considered setting standards and testing procedures for measuring drug release from topical creams and ointments. The proposed testing procedures would be analogous to current procedures that are used to test tablets and capsules for dissolution specifications.

The accepted apparatus employed and expected to be recommended by the FDA is the Franz cell (FIG. 1). In the Franz cell test aliquots are drawn manually at intervals from the side arm to determine the amount of drug release.

One proposed modification to the Franz cell is a device which automates the transfer of test aliquots from the cell. This device utilizes a six syringe pump to displace receptor media out of the cell and into the collection vial(s). While this device appears to be workable, it has several limitations and drawbacks. Because the device functions by displacing the receptor media in the cell it operates under pressure. Since previous studies of drug release from topical creams and ointments has involved testing under atmospheric pressures, comparisons between all previous work may not be possible when using a system that operates under pressure. In addition to providing results which are incompatible with all previous work, the use of a pressure operated system can cause serious reliability problems since any leaks will cause inconsistent collection of the test aliquots.

Furthermore, the use of syringe pumps involves minimum aliquots of about 1.2 ml due to the volume of fluid required to flush the delivery lines with the succeeding receptor media before an aliquot can be collected. This limitation reduces the concentration of the drug in the cell and impairs the delectability of very slightly soluble drugs.

An alternative approach is to provide a pump that is suitable for pumping the transfer fluid from the cell, through the collection head and back to the cell thus allowing the delivery lines to be to be flushed without and reducing the concentration of the drug in the cell. While peristaltic pumps have been used for this purpose, they have several operational drawbacks. For example, the precise volume delivered can be difficult to adjust when using a peristaltic pump. In addition, there are many drugs that are known to absorb on various tubing materials used in peristaltic pumps.

The present invention provides a pump which overcomes the disadvantages of the prior art.

DISCLOSURE OF THE INVENTION

It is accordingly one object of the present invention to provide a pump which has a minimum internal volume and operates at low pressures.

Another object of the present invention is to provide a diaphragm pump which has a minimum internal volume and a pumping capacity of one to several microliters per cycle.

It is another object of the present invention to provide a pump which is particularly useful in drug release testing systems.

A further object of the present invention is to provide an accurate, small capacity pump which is constructed with inert materials which will not absorb or react with a fluid which contacts the pump during use.

According to these and further objects of the present invention which will become apparent as the description thereof proceeds, the present invention provides for a diaphragm pump which includes:

a cylinder block having a cylinder bore formed therein;

a plunger provided in the cylinder bore for reciprocal movement therein, the plunger having an end which remains within the cylinder bore during the reciprocal movement;

a diaphragm which defines a deformable wall of a head cavity, the diaphragm being in fluid communication with the cylinder bore whereby fluid pressures within the cylinder bore act on the diaphragm to cause movement thereof; and at least one hydraulic fluid passage connected to the cylinder bore for supplying hydraulic fluid therein, the at least one hydraulic fluid passage being connected to the cylinder bore at a location at which the end of the plunger passes during the reciprocal movement thereof, whereby the plunger closes the at least one hydraulic fluid passage periodically during reciprocal movement of the plunger.

BRIEF DESCRIPTION OF DRAWINGS

The present invention will be described with reference to the attached drawings which are given by way of non-limiting examples only, in which.

BEST MODE FOR CARRYING OUT THE INVENTION

The present invention is directed to a diaphragm pump which includes a fluid actuated diaphragm that forms a displaceable wall of a head cavity. The head cavity is connected to a fluid line between opposed check valves in a conventional manner so that displacement of the diaphragm which forms the displaceable wall of the head cavity causes fluid to be pumped through the fluid line.

The present invention provides a unique design to drive the diaphragm in a reciprocating manner. In this regard, the present invention provides for pulses of fluid pressure to be applied to the side of the diaphragm which is opposed to the head cavity space. The present invention allows for uniform pressures to be applied to activate the diaphragm, which can be adjusted so as to provide displacement or pumped volumes of as low as 10 to 25 microliters for each stroke of the pump.

In a preferred embodiment, the structural elements of the pump are each made from materials which are inert, i.e. do not react with or absorb fluids which the pump is intended to contact during use. The pump structure is further designed so that two or more pumps can be ganged together or provided as an integral structure or unit which can be driven by a common-drive shaft/cam assembly. In this embodiment, the flow rate of each pump can be individually adjusted as described below so that the flow rate of all the pumps can be matched.

Figure 1:
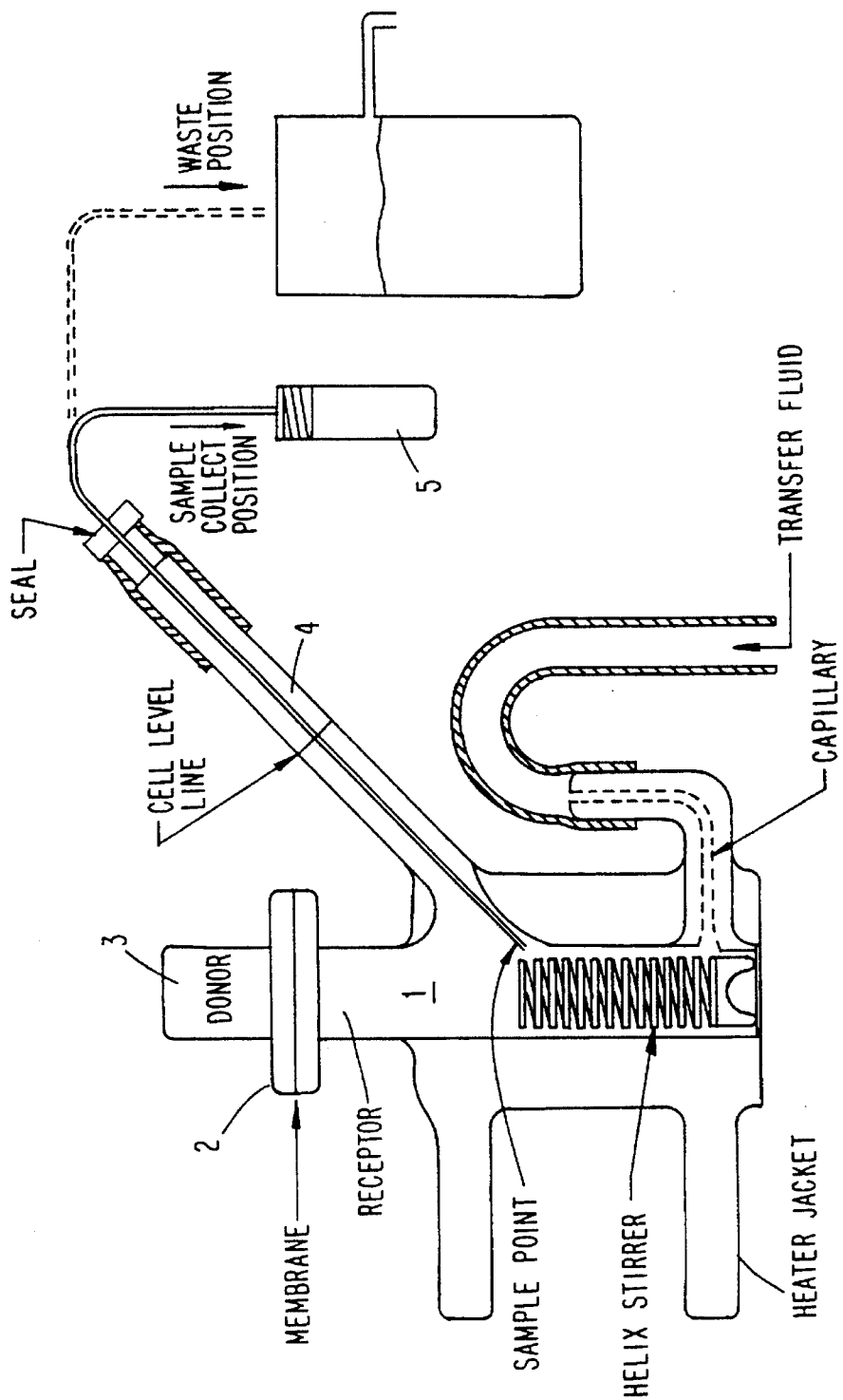
FIG. 1 is a schematic diagram of a conventional Franz cell.

The pumps of the present invention have been designed and developed to meet the needs of the volumetric pumping required by a conventional Franz cell. FIG. 1 is a schematic diagram of a Franz cell. In the Franz cell, the lower portion of the cell 1 is filled with a receptor media which contacts a membrane secured in a membrane holder 2. A donor media (sample) is provided in an upper portion of the cell 3 so that the donor fluid also contacts the membrane. The donor media (sample) contains a chemical species which is capable of passing through the membrane over time. The transfer of the chemical species through the membrane is determined by periodically sampling the receptor media in the lower portion of the cell 1 through the side arm 4. As discussed above, prior art systems utilized syringe pumps to displace samples of the receptor media out of the cell, through the side arm 4, and into the collection vial(s) 5. In order to test drug release from topical creams and ointments, the membrane is selected have characteristics which are similar to human skin, and the topical cream or ointment to be tested is used as the donor media (sample).

When used in conjunction with a Franz cell, the pump of the present invention can be used to displace samples of the receptor media out of the cell, through the side arm 4, and into the collection vial(s) 5.

It is of course to be understood that the pump of the present invention is not limited for use only with a Franz cell. In this regard, the pump can be utilized according to any pumping requirement, by merely scaling up (or down) the size of the pump. However, since one particular advantage of the pump of the present invention is for uniformly pumping extremely small volumes, e.g., as low as one to several microliters, the pump is particularly suitable for use in apparatuses like the Franz cell which require the transfer of small fluid volumes. According, for illustrative purposes, the pump design of the present invention will be described hereafter in conjunction with their use in Franz cells.

Figure 2:
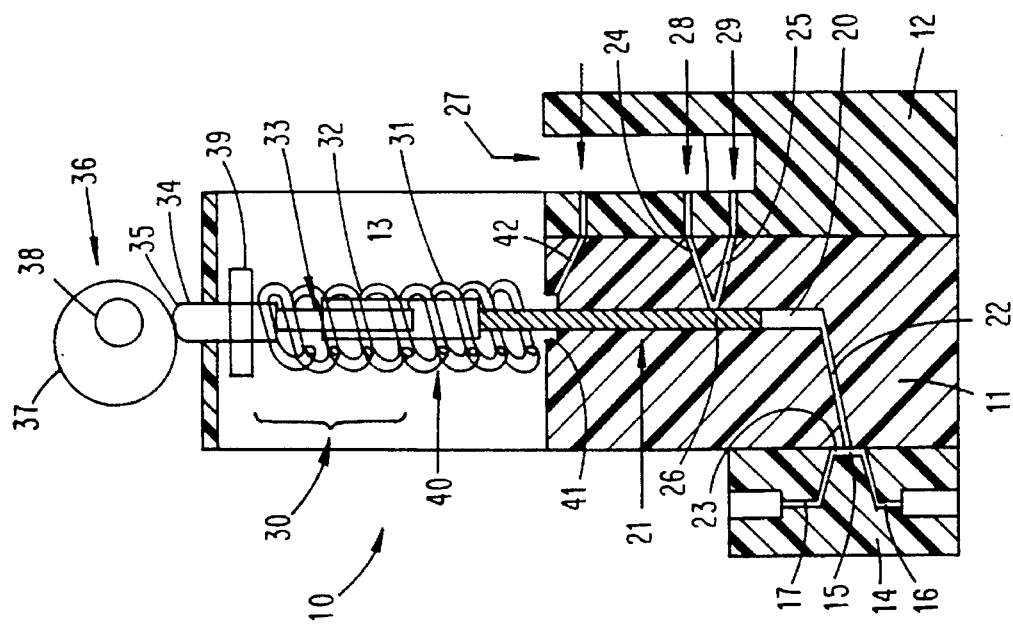
FIG. 2 is a schematic diagram of a pump according to the present invention.

FIG. 2 is a schematic diagram of a pump according to the present invention. The pump, which is generally indicated by reference numeral 10 includes a cylinder block 11, a reservoir 12 and a plunger section 13. In operation, a hydraulic fluid passed between the cylinder block 11 and the reservoir 12. Therefore, according to a preferred embodiment of the present invention, the cylinder block 11 and the reservoir 12 are integrally formed in order to prevent leaks of the hydraulic fluid. The plunger section 13 may also be integrally formed with the cylinder block 11 and the reservoir 12.

Figure 3:
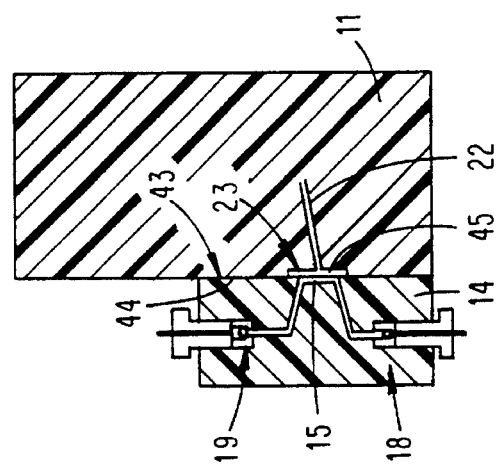
FIG. 3 is a schematic diagram of the pump chamber and the cylinder block which shows the position of the diaphragm.

A pumping chamber 14 is also shown in FIG. 2, The pumping chamber 14 includes a head cavity 15 which is connected by fluid passages 16 and 17 to an inlet check valve 18 and an outlet check valve 19 respectively (FIG. 3). The check valves can be ball check valves, flapper check valves, or any equivalent type of check valve. It is also possible to utilize stop valves which are automatically controlled to open and close so that a fluid can enter the head cavity 15 through one of the fluid passages and leave the head cavity through the other fluid passage in response to reciprocal motion of the diaphragm.

The cylinder block 11 includes a cylinder bore 20 which receives a plunger 21 therein. The cylinder bore 20 terminates into a fluid pressure transfer bore 22 which extends between the cylinder bore 20 and a diaphragm 23 which forms a displaceable wall of the head cavity 15 as discussed in detail below.

The plunger 21 has a limited, but adjustable distance in which it can travel within the cylinder bore 20. A hydraulic fluid vent passage 24 and a hydraulic fluid feed passage 25 are connected to the cylinder bore 20 at a point along the cylinder bore 20 at which the end of the plunger 21 can reciprocally pass during operation of the pump. As depicted, the hydraulic fluid vent passage 24 and the hydraulic fluid feed passage 25 are connected to the cylinder bore 20 at a common opening 26.

The opposite ends of the hydraulic fluid vent passage 24 and the hydraulic fluid feed passage 2 connect to a reservoir well 27 provided in the reservoir 12. The opposite ends of the hydraulic fluid vent passage 24 and the hydraulic fluid feed passage 25 form a hydraulic fluid vent port 28 and a hydraulic fluid feed port 29 which are located in a lower portion of the reservoir well 27. As shown in FIG. 2, the level of the hydraulic fluid in reservoir well 27 should be maintained between the hydraulic fluid vent port 28 and the hydraulic fluid feed port 29.

The upper portion of the plunger 21 is connected to an adjustable piston assembly 30 which extends beyond the plunger section 11. The adjustable piston assembly 30 includes a connector member 31 to Which the plunger 21 is attached. In order to attach the plunger 21 to the connector member 31, the connector member 31 can include a bore for receiving the plunger 21. The plunger 21 can be cemented, or otherwise fixed to or within the connector member 31 by any suitable means including a mechanical means such as a set screw, coacting threads, etc. Alternatively, the connector member 31 can be formed integrally with the plunger 21. In a preferred embodiment the connector member 31 is cylindrically shaped and coaxial with the plunger 21 as depicted.

The end or side of the connector member 31 which is opposite the plunger 21 includes an internally threaded bore 32 which receives a complementary threaded extension 33 of the upper piston member 34. As shown, the upper piston member 34 extends beyond the plunger section 11 and includes a smooth upper surface 35 which coacts with a cam driver 36 so as to reciprocally drive the plunger 21 along a stroke within the cylinder bore 20. The cam driver 36 includes a cam 37 which is rotated by a drive shaft 38.

The upper piston member 34 includes a flange 39 which functions both as a stop for the upper limit of the piston stroke when the flange 39 contacts the upper portion of the plunger section 13, and as a retainer for spring means 40 which applies a biasing force to the piston assembly 30 that causes the piston assembly 30 to retract the plunger 21 in the cylinder bore 20.

The cylinder block 11 includes a shallow well 41 in an upper surface thereof which is coaxial with and surrounds the cylinder bore 20. A hydraulic fluid seep return line 42 connects between the well 41 and an upper portion of the reservoir well 27. The well 41 is provided to collect any hydraulic fluid which is drawn upwards by the plunger 21 in the cylinder bore 20 and direct such hydraulic fluid to the seep return line 42.

FIG. 3 is a schematic diagram of the pump chamber 14 and the cylinder block 11 which shows the position of the diaphragm 23. As discussed above, the diaphragm 23 forms a displaceable wall of the head cavity 15. In order to provide this structure, one of the mating surfaces 43 and 44 of the pump chamber 14 and the cylinder block 11 includes a recess 45 for receiving the diaphragm 23 therein. The recess 45 is preferably provided in the mating surface 44 of the cylinder block 11 and has a depth that is slightly smaller than the thickness of the diaphragm 23 so that the edges of the diaphragm 23 can be compressed between the mating surfaces of the pump chamber 14 and the cylinder block 11 thereby forming a seal. In an alternative embodiment a gasket or sealing means such as an o-ring could be provided between the peripheral edge of the diaphragm 23 and one of the mating surfaces of the cylinder block 11 or the pump chamber 14. In a further embodiment, the diaphragm 12 could consist of a wall of the head cavity 15 which is molded and/or machined to be thin enough to undergo the desired deformation described above.

In operation, the reservoir well 27 is filled with a suitable hydraulic fluid, e.g. mineral oil, while the plunger 21 is held in an upper position in which the bottom of the plunger 21 is above the common opening 26 of the hydraulic fluid vent passage 24 and the hydraulic fluid feed passage 25. This manner of positioning the plunger 21 while filling the reservoir well 27 with hydraulic fluid allows the hydraulic fluid to fill the fluid pressure transfer bore 22 through the common opening 26 of the hydraulic fluid vent passage 24 and the hydraulic fluid feed passage 25.

Next, the plunger 21 is activated by depressing the upper piston member 34. This is preferably accomplished by contacting the smooth upper surface 35 of the upper piston member 34 with a cam driver 36 so as to reciprocally drive the plunger 21 along a stroke within the cylinder bore 20. As the plunger passes the common opening 26 of the hydraulic fluid vent passage 24 and the hydraulic fluid feed passage 25 on its downward movement, hydraulic fluid becomes trapped in the cylinder bore 20 below the plunger 21. Further downward movement of the plunger 21 creates pressure on the trapped hydraulic fluid which in turn causes the diaphragm 23 to deflect into the head cavity 15. As the diaphragm 23 deflects into the head cavity 15, fluid within the head cavity 15 and fluid passage 17 is forced to pass through the outlet check valve 19.

As the plunger 21 passes through the end of the plunger stroke, i.e., begins to move in the upward direction, the pressure on the trapped hydraulic fluid is reduced. This reduction in pressure causes the diaphragm 23 to be pulled out or retracted from the head cavity 15. At the same time, a fresh volume of fluid is pulled into The head cavity 15 by passing through the inlet check valve 18 and fluid passage 16.

As the plunger continues on its upward movement (by the biasing force of the spring means 40), the end of the plunger 21 passes the common opening 26 of the hydraulic fluid vent passage 24 and the hydraulic fluid feed passage 25. At this time, any hydraulic fluid which was lost during the previous plunger stroke is replaced with hydraulic fluid from the reservoir well 27. Such lost hydraulic fluid may include hydraulic fluid that seeps up the cylinder bore 20, between the plunger 21 and the inner surface of the cylinder bore 20. In addition, such lost hydraulic fluid may include hydraulic fluid that is lost through one or more small leaks that may develop over time.

The length of stroke of the piston can be adjusted by turning the threaded extension 33 of the upper piston member 35 with respect to the internally threaded bore of the connector member 31. This changes the length of the piston assembly 30.

The structural elements of the pump are preferably made from materials which are inert, i.e. do not react with or absorb fluids which the pump is intended to contact during use. For example, the cylinder block 11, reservoir 12, plunger section 13, and pump chamber 14 are preferably made from polytetrafluoroethylene (PTFE) or a similar inert plastic. Alternatively, the cylinder block 11, reservoir 12, plunger section 13, and pump chamber 14 could be made from an inert metal such as stainless steel. The plunger 21 should be made out of an inert metal such as stainless steel or a suitable strong plastic such as PTFE which can be smoothed to resist wear due to friction. The diaphragm 23 can be and from an inert material that is consistently deformable. In a preferred embodiment a PTFE diaphragm was utilized and found to be suitable for purposes of the present invention. When using ball check valves as the inlet and outlet check valves 18 and 19, PTFE valve seats and stainless steel balls should be utilized.

The pump structure is designed so that two or more pumps can be ganged together or provided as an integral structure or unit. In this regard, it should be apparent that the cylinder block 11, reservoir 12, plunger section 13, and pump chamber 14 can each be in the shape of blocks that can be easily attached together by suitable mechanical means such as through-bolts and used in conjunction with a common drive shaft/cam assembly. Alternatively, a single cylinder block, reservoir, plunger section, and pump chamber could be provided with a plurality of the necessary cylinder bores, plungers, piston assemblies, reservoir wells, etc. so as to provide an integral unit that includes an array of pumps.

As can be appreciated, the pump of the present invention is not limited by size or utility. In a preferred embodiment which was designed to be used in conjunction with a Franz cell, the pump was sized to displace between 10 and 25 microliters per plunger stroke and to operate at a pumping frequency of one stroke per second. When properly sized, the pump design of the present invention can be used as a substitute for almost any type of pump, including peristaltic pumps, other diaphragm pumps, piston pumps, or the like.

Although the present invention has been described with reference to particular means, materials and embodiments, from the foregoing description, one skilled in the art can ascertain the essential characteristics of the present invention and various changes and modification may be made to adapt the various uses and characteristics thereof without departing from the spirit and scope of the present invention as describe in the claims which follow.

I claim:

1. A diaphragm pump which comprises:

a cylinder block having a cylinder bore formed therein;

a plunger provided in said cylinder bore for reciprocal movement therein, said plunger having an end which remains within said cylinder bore during the reciprocal movement;

a diaphragm which defines a deformable wall of a head cavity, said diaphragm being in fluid communication with said cylinder bore whereby fluid pressures within said cylinder bore act on said diaphragm to cause movement thereof;

two hydraulic fluid passages which connect to said cylinder bore at a common point at which said end of said plunger passes during the reciprocal movement thereof, whereby said plunger closes said two hydraulic fluid passages periodically during reciprocal movement of said plunger;

inlet and outlet fluid passages connected to said head cavity; and check valves provided in said inlet and outlet fluid passages.

2. A diaphragm pump which comprises:

a cylinder block having a cylinder bore formed therein;

a plunger provided in said cylinder bore for reciprocal movement therein, said plunger having an end which remains within said cylinder bore during the reciprocal movement;

a diaphragm which defines a deformable wall of a head cavity, said diaphragm being in fluid communication with said cylinder bore whereby fluid pressures within said cylinder bore act on said diaphragm to cause movement thereof;

at least one hydraulic fluid passage connected to said cylinder bore for supplying hydraulic fluid therein, said at least on hydraulic fluid passage being connected to said cylinder bore at a location at which said end of said plunger passes during the reciprocal movement thereof, whereby said plunger closes said at least one hydraulic fluid passage periodically during reciprocal movement of said plunger;

a hydraulic fluid reservoir for storing a hydraulic fluid, said at least one hydraulic fluid passage being in fluid communication with said hydraulic fluid reservoir;

a coaxial well provided at an upper portion of said cylinder bore, said well being connected by a fluid passage to an upper portion of said hydraulic fluid reservoir;

inlet and outlet fluid passages connected to said head cavity; and check valves provided in said inlet and outlet fluid passages.

* * * * *